(12) United States Patent
Keiichi

(10) Patent No.: US 7,125,960 B2
(45) Date of Patent: Oct. 24, 2006

(54) CROSSLINKED ELASTIN AND PROCESS FOR PRODUCING THE SAME

(75) Inventor: Miyamoto Keiichi, Hisai (JP)

(73) Assignee: Chisso Corporation, Osaka (JP)

(*) Notice: Subject to any disclaimer, the term of this patent is extended or adjusted under 35 U.S.C. 154(b) by 38 days.

(21) Appl. No.: 10/478,150

(22) PCT Filed: May 30, 2002

(86) PCT No.: PCT/JP02/05275

§ 371 (c)(1),
(2), (4) Date: Nov. 19, 2003

(87) PCT Pub. No.: WO02/96978

PCT Pub. Date: May 12, 2002

(65) Prior Publication Data

US 2004/0136977 A1    Jul. 15, 2004

(30) Foreign Application Priority Data

May 30, 2001    (JP) ............... 2001-163505

(51) Int. Cl.
  C07K 1/08     (2006.01)
  C12N 9/64     (2006.01)
  C08G 63/48    (2006.01)
  C08G 63/91    (2006.01)

(52) U.S. Cl. ............... 530/350; 530/402; 424/484; 424/422; 525/54.1; 435/226

(58) Field of Classification Search ........ 530/350–356, 530/396, 395, 402; 602/41–46; 424/422, 424/484; 525/54.1; 435/226
See application file for complete search history.

(56) References Cited

U.S. PATENT DOCUMENTS 4,755,593 A * 7/1988 Lauren ............... 530/356

FOREIGN PATENT DOCUMENTS

| JP | 08-033661 | 2/1996 |
| JP | 09-173361 | 7/1997 |
| JP | 09-273080 | 10/1997 |
| WO | WO 89/00413 | 1/1989 |
| WO | WO 96/34618 | 11/1996 |

OTHER PUBLICATIONS

Courtman, D.W., Pereira, C.A., et al. 1994. Development of a pericardial acellular matrix biomaterial: Biochemical and mechanical effects of cell extraction. J. Biomed. Mat. Res. 28: 655-666.*

* cited by examiner

Primary Examiner—Karen Cochrane Carlson
Assistant Examiner—Marsha Tsay
(74) Attorney, Agent, or Firm—Ohlandt, Greeley, Ruggiero & Perle, LLP

(57) ABSTRACT

A crosslinked elastin, a water-soluble crosslinking agent to be used for crosslinking, molded elastin articles, medical instruments and regeneration tissues using the crosslinked elastin, and a surgical therapy method and regeneration treatment wherein the medical instruments are employed. There is provided a biocompatible functional material having elasticity suitable for transplantation into the body without causing detachment of cell adhesion proteins.

13 Claims, 15 Drawing Sheets
(12 of 15 Drawing Sheet(s) Filed in Color)

Elastin:Gelatin = 0:100    Elastin:Gelatin = 1:99    Elastin:Gelatin = 10:90    Elastin:Gelatin = 90:10

CROSSLINKED ELASTIN AND PROCESS FOR PRODUCING THE SAME

This application claims priority from Application Serial No. 2001-163,505, Filed on May 30, 2001 in Japan. This application also claims priority from PCT International Patent Application No. PCT/JP02/05275, Filed on May 30, 2002 and published on Dec. 5, 2002 as WO 02/096978 A1. The contents of the preceeding applications are incorporated herein by reference as fully set forth herein for all purposes.

FIELD OF THE INVENTION

The present invention relates to a biocompatible functional material, and to its production process, medical instruments, crosslinking agents, surgical therapy methods and regeneration tissue.

DISCUSSION OF THE BACKGROUND ART

One method used to treat patients with severed nerve tissue resulting from accidents, disasters and other causes has been to ligate tubes made of artificial materials to the site of nerve deficiency to induce regeneration of nerve tissue in the tube. The tubes used have interiors of silicone, polyurethane, polyester, polyethylene terephthalate, alginic acid, polylactic acid or the like, coated with a cell adhesion protein such as collagen or laminin.

As a therapy method for patients with severed blood vessels, a fabric composed of knitted synthetic polymer fibers made of silicone, polyurethane, polyester or the like is formed into a tube, and the inside is coated with a cell adhesion protein such as collagen or laminin to prepare an artificial blood vessel which is transplanted into the site of the severed blood vessel to induce endothelial cells into the artificial blood vessel.

SUMMARY OF THE INVENTION

In the therapy method described above, the silicone tubes or polyurethane tubes or artificial blood vessels are coated with cell adhesion proteins such as collagen or laminin, but since the inner surfaces of the tubes have no cell adhesion properties, the cell adhesion proteins become detached with extended therapy resulting in inadequate regeneration of the nerve or blood vessel tissue.

Tubes or artificial blood vessels transplanted into an animal must be elastic so as to follow the movement of the body or tissue, but because tubes or artificial blood vessels composed mainly of silicone or polyester have a Young's modulus (elastic modulus) of $1 \times 10^7$ Pa or greater as compared to the Young's modulus (elastic modulus) of $1 \times 10^4$ to $2 \times 10^6$ Pa for the accommodating tissue, the joint is therefore subjected to high stress and can lead to such problems as thrombosis. Materials with the same elasticity as human tissue have therefore been desired.

As a result of diligent research conducted in the light of these problems of the prior art, the present inventors have found that by crosslinking a water-soluble elastin with a crosslinking agent it is possible to obtain a crosslinked elastin having elasticity suitable for transplantation into the body while avoiding detachment of the coated cell adhesion proteins such as collagen or laminin, and the present invention has been completed on the basis of this finding.

The invention has the following construction.

(1) A crosslinked elastin comprising a crosslinking starting material containing at least one type of water-soluble elastin crosslinked with a water-soluble crosslinking agent.

(2) A crosslinked elastin according to (1), wherein the crosslinking starting material further comprises one or more components selected from among proteins such as collagen, gelatin, fibronectin, fibrin, laminin, casein, keratin, sericin and thrombin, polyamino acids such as polyglutamic acid and polylysine, sugars such as polygalacturonic acid, heparin, chondroitin sulfate, hyaluronic acid, dermatan sulfate, chondroitin, dextran sulfate, sulfated cellulose, alginic acid, dextran, carboxymethylchitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan and lentinan, cell growth factors such as bFGF (basic Fibroblast Growth Factor), TGF-α (Transforming Growth Factor α), EGF (Epidermal Growth Factor), VEGF (Vascular Endothelial Growth Factor) and CNTF (Ciliary NeuroTrophic Factor), as well as polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid.

(3) A crosslinked elastin according to (1), wherein the water-soluble elastin content is in the range of 0.5–99.5 wt %.

(4) A crosslinked elastin according to (1), wherein the Young's modulus is in the range of $1 \times 10^2$ to $1 \times 10^7$ Pa.

(5) A crosslinked elastin according to (1), wherein the internal structure is a porous sponge structure.

(6) A crosslinked elastin according to (5), wherein the mean diameter of the pores is less than 20 μm.

(7) A crosslinked elastin according to (5), wherein the mean diameter of the pores is in the range of 20 μm to 2 mm.

(8) A crosslinked elastin according to (1) or (2), wherein the one or more components selected from among proteins such as collagen, gelatin, fibronectin, fibrin, laminin, casein, keratin, sericin and thrombin, polyamino acids such as polyglutamic acid and polylysine, sugars such as polygalacturonic acid, heparin, chondroitin sulfate, hyaluronic acid, dermatan sulfate, chondroitin, dextran sulfate, sulfated cellulose, alginic acid, dextran, carboxymethylchitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan and lentinan, cell growth factors such as bFGF (basic Fibroblast Growth Factor), TGF-α (Transforming Growth Factor α), EGF (Epidermal Growth Factor), VEGF (Vascular Endothelial Growth Factor) and CNTF (Ciliary NeuroTrophic Factor), as well as polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid, are chemically bonded.

(9) A crosslinked elastin according to (8), wherein the chemical bond is a crosslink produced using a crosslinking agent.

(10) A crosslinked elastin according to (1), (2) or (8), which comprises one or more components selected from among proteins such as collagen, gelatin, fibronectin, fibrin, laminin, casein, keratin, sericin and thrombin, polyamino acids such as polyglutamic acid and polylysine, sugars such as polygalacturonic acid, heparin, chondroitin sulfate, hyaluronic acid, dermatan sulfate, chondroitin, dextran sulfate, sulfated cellulose, alginic acid, dextran, carboxymethyl-chitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan and lentinan, cell growth factors such as bFGF (basic Fibroblast Growth Factor), TGF-α (Transforming Growth Factor α), EGF (Epidermal Growth Factor), VEGF (Vascular Endothelial Growth Factor) and CNTF (Ciliary NeuroTrophic Factor), as well as polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid.

(11) A crosslinked elastin according to (1), wherein the water-soluble crosslinking agent is a water-soluble compound having a hydrophobic portion in the center region of the molecule and having an amino group-reacting active ester group at both ends.

(12) A crosslinked elastin according to (1), characterized in that the water-soluble crosslinking agent is a water-soluble compound represented by the following general formula.

<General formula>

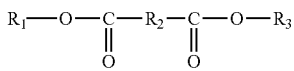

[wherein $R_1$ and $R_3$ are each <A> or <B> represented by the following structural formulas and $R_1$ and $R_3$ may be the same or different:

A

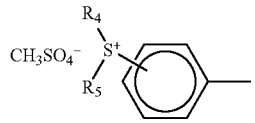

(wherein $R_4$ and $R_5$ are each H, $CH_3$ or $C_2H_5$, and $R_4$ and $R_5$ may be the same or different);

B

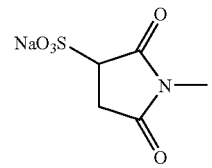

and $R_2$ is <C> or <D> represented by the following structural formulas:

<C>

(wherein n is an integer of 1–20);

D

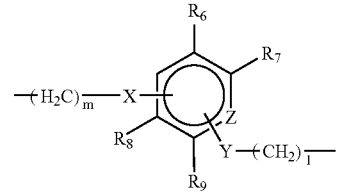

(wherein m and 1 are each an integer of 0–15, X and Y are each $CH_2$ or O and X and Y may be the same or different, Z is C or N, and $R_6$, $R_7$, $R_8$ and $R_9$ are each H, $CH_3$ or $C_2H_5$ and may be the same or different).]

(13) A molded elastin article made from a crosslinked elastin according to any one of (1) to (12).

(14) A molded elastin article according to (13), wherein the shape is filamentous, membranous, cylindrical, pelleted or tubular.

(15) A medical instrument employing a crosslinked elastin according to (1).

(16) A surgical therapy method characterized by utilizing a medical instrument according to (15).

(17) A regeneration treatment characterized by utilizing a crosslinked elastin according to (1) or a medical instrument according to (15).

(18) Regeneration tissue obtained using a crosslinked elastin according to (1).

(19) A crosslinking agent comprising a water-soluble compound having a hydrophobic portion in the center region of the molecule and having an amino group-reacting active ester group at both ends.

(20) A crosslinking agent according to (19), wherein the compound is a compound represented by the following general formula.

<General formula>

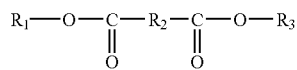

[wherein $R_1$ and $R_3$ are each <A> or <B> represented by the following structural formulas and $R_1$ and $R_3$ may be the same or different:

A

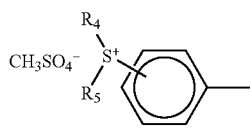

(wherein $R_4$ and $R_5$ are each H, $CH_3$ or $C_2H_5$, and $R_4$ and $R_5$ may be the same or different);

B

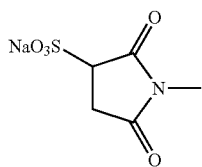

and $R_2$ is <C> or <D> represented by the following structural formulas:

<C>

$-(CH_2)_n-$ (wherein n is an integer of 1–20);

<D>

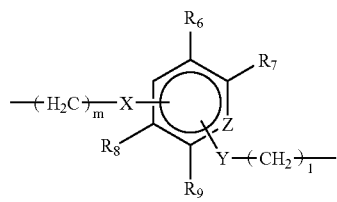

(wherein m and l are each an integer of 0–15, X and Y are each $CH_2$ or O and X and Y may be the same or different, Z is C or N, and $R_6$, $R_7$, $R_8$ and $R_9$ are each H, $CH_3$ or $C_2H_5$ and may be the same or different).]

(21) A production process of crosslinked elastin, characterized by crosslinking a water-soluble elastin by crosslinking reaction using a water-soluble crosslinking agent according to (19).

(22) A production process of crosslinked elastin according to (21), characterized in that the reaction temperature for the crosslinking reaction is in the range of 4–150° C.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
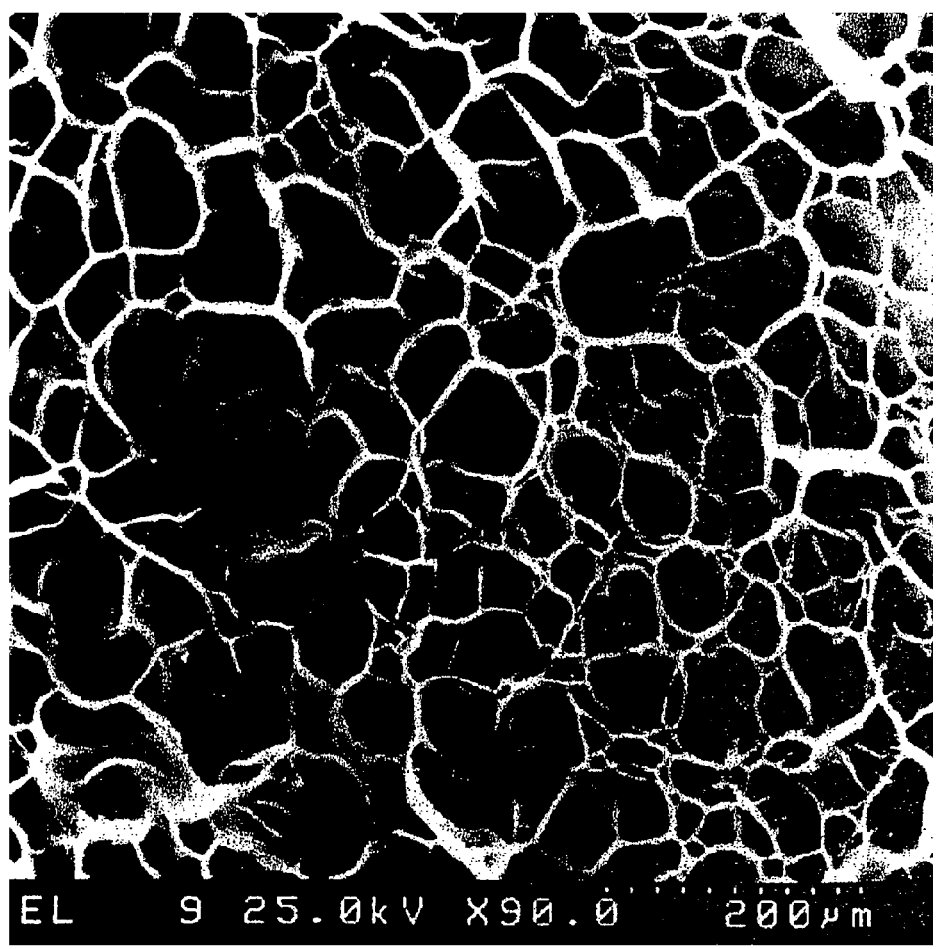
FIG. 1 is an electron micrograph of the crosslinked elastin of the invention according to Example 8 (25° C. reaction).

The water-soluble elastin used for the invention is not particularly restricted and may be obtained by hydrolysis. Specifically, there may be used at least one type of elastin selected from among α-elastin or β-elastin obtained by hot oxalic acid treatment of animal cervical ligament or the like, K-elastin obtained by alkali ethanol treatment of elastin, water-soluble elastin obtained by enzyme treatment with elastase, and tropoelastin which is the precursor in the elastin biosynthesis pathway. There are no particular restrictions on tropoelastin, and it may be any one or more types from among extracts from animal cells and tropoelastin gene products obtained by gene recombination.

Elastin is an elastic protein normally found in the body, and abundantly found in body tissues which require elasticity, such as arteries and vocal cords. Elastin present in the body is water-insoluble due to a high content of hydrophobic amino acids and rigid crosslinked structures such as desmosine and isodesmosine. Such elastin exhibits an elastic property as a result of unique structures known as "oiled coils" created by the crosslinking.

The crosslinked elastin of the present invention may be obtained by using a water-soluble crosslinking agent to crosslink one or more types of water-soluble elastin rendered water-soluble by degradation of the crosslinked structure of biogenic elastin. Molded elastin articles of the invention may be obtained by combining the aforementioned water-soluble elastin and water-soluble crosslinking agent to prepare a water-soluble aqueous elastin solution, and then casting it onto a molding template or the like, heating and so forth to accomplish crosslinking.

The crosslinked elastin of the invention may also comprise a third component in addition to the water-soluble elastin and crosslinking agent. Such a third component is not particularly restricted. As examples of third components there may be mentioned proteins such as collagen, gelatin, fibronectin, fibrin, laminin, casein, keratin, sericin and thrombin, polyamino acids such as polyglutamic acid and polylysine, sugars such as polygalacturonic acid, heparin, chondroitin sulfate, hyaluronic acid, dermatan sulfate, chondroitin, dextran sulfate, sulfated cellulose, alginic acid, dextran, carboxymethylchitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan and lentinan, cell growth factors such as bFGF (basic Fibroblast Growth Factor), TGF-α (Transforming Growth Factor α), EGF (Epidermal Growth Factor), VEGF (Vascular Endothelial Growth Factor) and CNTF (Ciliary NeuroTrophic Factor), as well as compounds such as polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid. Incorporation of one or more such components will cause no problem. Particularly preferred are extracellular matrix components such as collagen, gelatin, fibronectin, laminin, heparin and chondroitin sulfate or cell growth factors such as bFGF (basic Fibroblast Growth Factor), for enhanced cell adhesion and growth.

The proportion of water-soluble elastin in the crosslinked elastin of the invention is preferably in the range of 0.5–99.5 wt % with respect to the crosslinked elastin. The range is more preferably 1–95%, since this range will give satisfactorily moldable molded articles with biocompatible elasticity.

The water-soluble elastin is a hydrophobic protein of which approximately 94% of the total weight consists of hydrophobic amino acids and approximately 1% consists of amino acids with amino groups on the side chain (lysine, arginine, histidine). The water-soluble crosslinking agent used for the invention may be any water-soluble crosslinking agent which reacts with the side chain amino groups of the water-soluble elastin to accomplish crosslinking reaction. As examples of water-soluble crosslinking agents there may be mentioned glutaraldehyde, ethyleneglycidyl ether and the like, or compounds having a hydrophobic portion in the center region of the molecule and having an active ester group at both ends, as represented by the general formula shown below. A compound represented by the following general formula is preferably used as the crosslinking agent in order to yield satisfactorily shapeable molded articles with biocompatible elasticity.

<General formula>

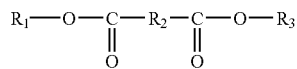

[wherein $R_1$ and $R_3$ are each <A> or <B> represented by the following structural formulas and $R_1$ and $R_3$ may be the same or different:

A

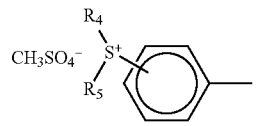

(wherein $R_4$ and $R_5$ are each H, $CH_3$ or $C_2H_5$, and $R_4$ and $R_5$ may be the same or different);

B

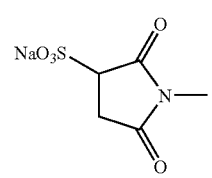

$R_2$ is <C> or <D> represented by the following structural formulas:

<C>

(wherein n is an integer of 1–20);

D

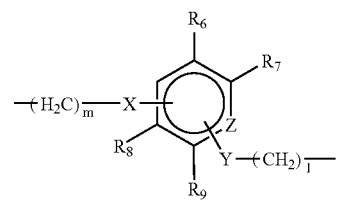

(wherein m and l are each an integer of 0–15, X and Y are each $CH_2$ or O and X and Y may be the same or different, Z is C or N, and $R_6$, $R_7$, $R_8$ and $R_9$ are each H, $CH_3$ or $C_2H_5$ and may be the same or different).]

Compounds having a hydrophobic portion in the center region of the molecule form rigid, stable structures with hydrophobic amino acid-rich elastin by hydrophobic interaction. However, although compounds with numerous hydrophobic portions are soluble in organic solvents, they are sparingly or totally insoluble in water and thus poorly manageable in aqueous systems. The water-soluble crosslinking agent of the invention is characterized by having both ends of the dicarboxylic acid compound represented by the above-mentioned general formula converted to an active ester with 4-hydroxyphenyldimethyl-sulfonium methylsulfate (DSP), and by having a hydrophobic portion which forms a rigid, stable structure with hydrophobic amino acid-rich elastin, while dissolving in water and thus being manageable in an aqueous system.

The active ester groups at both ends in the chemical formula of the water-soluble crosslinking agent of the invention form peptide bonds with amino acids of the water-soluble elastin, thus producing crosslinks. The crosslinked elastin obtained by crosslinking with the water-soluble crosslinking agent of the invention is therefore characterized by being highly biodegradable in the body. The biodegradation rate depends on the degree of crosslinking of the crosslinked elastin, and may therefore be controlled by varying the crosslinking conditions to alter the degree of crosslinking.

The structure of the crosslinked elastin of the invention is not particularly restricted, but is preferably a porous sponge structure so as to allow penetration of body fluids, culture solutions and the like. Although there are no particular restrictions on the sizes of the pores, a mean diameter of less than 20 μm will tend to yield a hard crosslinked product with a high Young's modulus (elastic modulus). On the other hand, a range of 20 μm to 2 mm will tend to yield a moldable crosslinked product with a low Young's modulus (elastic modulus) and a high degree of swelling.

The crosslinked elastin of the invention is a highly elastic crosslinked product, and for greater biocompatibility it preferably has a Young's modulus (elastic modulus) in the range of $1\times10^2$ to $1\times10^7$ Pa, and more preferably in the range of $1\times10^3$ to $2\times10^6$ Pa.

There are no particular restrictions on the shape of a molded elastin article according to the invention, but for medical applications it is preferably filamentous, membranous, cylindrical, pelleted or tubular.

The crosslinked elastin of the invention may form a specific structure by itself, or it may form a complex with components other than the crosslinked elastin. Surface coatings with structures other than that of the crosslinked elastin may also be used. Components forming such complexes are not particularly restricted, and as examples there may be mentioned proteins such as collagen, gelatin, fibronectin, fibrin, laminin, casein, keratin, sericin and thrombin, polyamino acids such as polyglutamic acid and polylysine, sugars such as polygalacturonic acid, heparin, chondroitin sulfate, hyaluronic acid, dermatan sulfate, chondroitin, dextran sulfate, sulfated cellulose, alginic acid, dextran, carboxymethylchitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan and lentinan, cell growth factors such as bFGF (basic Fibroblast Growth Factor), TGF-α (Transforming Growth Factor α), EGF (Epidermal Growth Factor), VEGF (Vascular Endothelial Growth Factor) and CNTF (Ciliary NeuroTrophic Factor), as well as compounds such as polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid. Any one or more of these may be used to confer biofunctional properties such as cell adhesion or antithrombotic activity not possessed by the elastin, or to increase the growth rate of the tissue of interest.

The conditions for the crosslinking reaction between the water-soluble elastin and water-soluble crosslinking agent are not particularly restricted, but the reaction temperature is preferably in the range of 4–150° C. at ordinary pressure or under pressurization with an autoclave or the like. A range of 10–120° C. is particularly preferred from the standpoint of manipulation of the crosslinking. When the crosslinked elastin of the invention has a porous sponge structure, the reaction temperature may be controlled to allow control of the pore diameters. For example, a reaction temperature in the range of 4–50° C. can yield crosslinked products with pore mean diameters of 20 μm and greater, while a temperature in the range of 50–150° C. can yield crosslinked products with pore mean diameters of less than 20 μm.

The method of molding the crosslinked elastin of the invention is not particularly restricted, and a molding die commonly used for molding of synthetic resins may be used. For example, the water-soluble elastin and the water-soluble crosslinking agent of the invention may be combined and the resulting water-soluble elastin aqueous solution may be cast into a molding machine and heated with an autoclave or the like for crosslinking, to produce crosslinked elastin having a filamentous, membranous, cylindrical, pelleted or tubular shape reflecting that of the die.

Because the crosslinked elastin of the invention has elasticity in the same range as that of living tissue, it has excellent stretchability and can be effectively used for cosmetics and medical instruments. It is not particularly restricted in its uses for cosmetics and may serve, for example, as a face mask base for skin care products. There are also no particular restrictions on its uses for medical instruments, and application for molding of parts such as catheters, shunts, wound coverings and the like may provide more flexible functions than have existed in the prior art.

When a medical instrument of the invention employing such materials as regeneration treatment materials is implanted into the body, the tissue of interest will grow more favorably in the body. Such use is particularly effective for neurons and blood vessels, as mentioned above.

In order to further increase the cell growth rate and improve biocompatibility, the crosslinked elastin may be combined with third components to confer functions not naturally exhibited by elastin. For example, there may be included cell growth factors or heparin, which is antithrombotic and interacts with cell growth factors.

Such third components may be premixed with the starting material during formation of the crosslinked elastin for incorporation into the crosslinked product, or the crosslinked elastin may be formed first and the third components impregnated into the structure or physically adsorbed onto it after drying. Alternatively, the third components may be chemically anchored to the crosslinked elastin in order to inhibit their loss.

The crosslinked elastin of the invention may be used as a sustained release carrier, which is a type of drug delivery system (DDS). In particular, the crosslinked elastin of the invention can yield porous sponge structures with a high Young's modulus (elastic modulus), and can exhibit a curative effect on nerves, blood vessels and the like.

A medical instrument according to the invention has the function and effect described above, and is therefore particularly effective when used for surgical therapy. For example, collagen sheets having coagulants such as fibrin or thrombin anchored on one side thereof are currently used as postoperative hemostatic adhesives. Here, sites of visceral hemorrhage created by surgery are covered with the sheets, with the goal of achieving the synergetic effect of hemostasis by blood clotting components and hemostasis by the physical compression with the collagen sheet, as well as greater handling ease, but collagen sheets have poor stretchability and have therefore exhibited low contact bonding properties when utilized in vigorously moving organs such as the heart. By using a crosslinked elastin sheet according to the invention, however, it is possible to produce a sheet with high stretchability which can adapt to organ movement. In addition, a complex between the crosslinked elastin of the invention and collagen may be formed to produce a very highly biocompatible sheet characterized by exhibiting both the stretchability of elastin and the cell adhesion properties of collagen.

While the crosslinked elastin of the invention may be implanted in the body as described above for utilization as a scaffold for regeneration of blood vessels or nerves, its function can also be utilized outside of the body. Specifically, it may be used as a culturing substrate for regeneration medicine, whereby organs of a desired form can be formed by transplantation and culturing of direction-oriented embryonic stem (ES) cells, somatic stem cells, mesenchymal stem cells and the like either on a sheet surface or inside a tube according to the invention. The crosslinked elastin of the invention not only has satisfactory moldability but is also biodegradable, and therefore is useful for providing a cartridge-type regeneration treatment method and regeneration tissue whereby organs which have been partly cultured to shape formation may be transplanted together with the culturing substrate.

EXAMPLES

The present invention will now be explained in greater detail through the following examples. Unless otherwise specified, the "%" values are based on weight.

Example 1

Preparation of Water-Soluble Elastin

After adding 150 ml of 0.25 M oxalic acid to 20 g of powdered water-insoluble elastin (product of Elastin Products Company, Inc), the mixture was treated at 100° C. for 1 hour. After cooling, it was centrifuged (3000 rpm, 30 min) to separation, the supernatant was collected and placed in a cellulose dialysis tube (molecular cutoff: 6000–10,000), and dialysis was performed for 48 hours against deionized water to remove the oxalic acid. This was followed by lyophilization to obtain water-soluble elastin. The amino acid analysis results for the elastin starting material and the water-soluble elastin are shown in Table 1.

TABLE 1

|  | Elastin (mol %) | Water-soluble elastin (mol %) |
| --- | --- | --- |
| Aspartic acid | 0.612 | 0.542 |
| Threonine | 0.778 | 0.983 |
| Serine | 0.665 | 0.964 |
| Glutamic acid | 1.668 | 1.923 |
| Glycine | 33.22 | 30.869 |
| Alanine | 22.78 | 25.512 |
| Cysteine | 0.376 | 0.562 |
| Valine | 13.374 | 12.652 |
| Isoleucine | 2.568 | 2.249 |
| Leucine | 6.235 | 6.001 |
| Tyrosine | 0.703 | 0.976 |
| Phenylalanine | 2.967 | 3.023 |
| Lysine | 0.279 | 0.381 |
| Histidine | 0.037 | 0.063 |
| Arginine | 0.516 | 0.68 |
| Hydroxyproline | 1.168 | 1.007 |
| Proline | 11.699 | 11.612 |
| Total | 100.00 | 100.00 |

Example 2

Production of Crosslinked Elastin Using Glutaraldehyde as Crosslinking Agent

A 90 mg portion of the water-soluble elastin obtained in Example 1 was added to and dissolved in 161 µl of deionized water to obtain a water-soluble elastin aqueous solution. To this aqueous solution there was added 48.7 µl of 250 mM aqueous glutaraldehyde (product of Tokyo Kasei Kogyo Co., Ltd.), immediately producing a crosslinked elastin gel. It was attempted to cast the crosslinked elastin gel into a cylindrical molding template with a 2 mm diameter and 2 cm length, but the fluidity was too poor to allow casting. Casting into the template was difficult even when the amount of 250 mM aqueous glutaraldehyde addition was reduced to ¹⁄₁₀ the previous amount.

Example 3

Production of Crosslinked Elastin Using Ethyleneglycol Diglycidyl Ether as Crosslinking Agent A 36 mg portion of the water-soluble elastin obtained in Example 1 was added to and dissolved in 41.6 µl of deionized water to obtain a water-soluble elastin aqueous solution. To this aqueous solution there was added 42.4 µl of 287 mM aqueous ethyleneglycol diglycidyl ether, and upon thorough mixing, the solution was cast into a cylindrical template with a 2 mm diameter and 2 cm length and heated at 50° C. for one hour to obtain a crosslinked elastin gel. The obtained crosslinked elastin gel was thoroughly washed with deionized water, and upon conducting a simple stretching test by pulling with the fingers at both ends, it was found to be fragile against stretching deformation.

Example 4

Production of Crosslinked Elastin Using Water-Soluble Carbodiimide as Crosslinking Agent A 50 mg portion of the water-soluble elastin obtained in Example 1 was added to and dissolved in 10.4 μl of deionized water to obtain a water-soluble elastin aqueous solution. To this aqueous solution there was added 10.4 μl of 274 mM water-soluble carbodiimide (WSCD, product of Peptide Institute, Inc.), and after further adding 24.4 μl of 645 mM adipic acid the mixture was thoroughly agitated to obtain a 30% aqueous elastin solution. Long-chain dicarboxylic acids do not dissolve in deionized water (they will dissolve under alkali conditions but then are highly reactive with carbodiimide), and therefore incomplete dissolution and partial solidification occurred as expected, making it impossible to accomplish casting in different templates (glass tubes, membrane-forming dies, etc.).

Example 5

Production of Crosslinked Elastin Using Photoreactive Succinimide Ester as Crosslinking Agent A 13 mg portion of the water-soluble elastin obtained in Example 1 and 4 mg of a photoreactive succinimide ester (NHS-ASA: N-hydroxysuccinimidyl-4-azidosalicylic acid, product of PIERCE) were added to and dissolved in 1 ml of deionized water and reacted at room temperature for one day. After completion of the reaction, the unreacted portion was removed and the product was purified to obtain 7 mg of photoreactive elastin. To this there was added 20 μl of deionized water to prepare a photoreactive aqueous elastin solution, and 365 nm ultraviolet (UV) irradiation for 90 minutes produced a gel. The obtained gel was thoroughly washed with deionized water. As a result, because the crosslinking agent was water-insoluble it exhibited low reactivity, while the elastin was insolubilized in the organic solvent and thus also exhibited poor reactivity. With photoirradiation, the UV rays penetrated with a low aqueous elastin solution concentration (a few percent), but at concentrations of 10% or greater, reaction only occurred on the light irradiation surface and therefore the gelling was poor and reaction was virtually impossible in a template.

Example 6

Production of Crosslinked Elastin Using Adipic Acid Succinimide Ester as Crosslinking Agent After adding and dissolving 60 mg of the water-soluble elastin obtained in Example 1 in 119 μl of deionized water, 21 μl of 385 mM aqueous adipic acid succinimide ester was added, and the solution was cast into a cylindrical template with a 2 mm diameter and 2 cm length and heated at 80° C. for one hour to obtain a gel. The produced gel was weak (it did not form the shape of the template), possibly due to partial insolubilization of the crosslinking agent. The dodecanedicarboxylic acid succinimide ester was insoluble in water and was therefore unreactive.

Example 7

Production of Water-Soluble Crosslinking Agent [A]

The carboxyl groups of a dicarboxylic acid were converted to active esters with 4-hydroxyphenyldimethylsulfonium methylsulfate (DSP). The active esterification with DSP was carried out in the following experiment following a method reported in the field of peptide chemistry (K. Kouge, T. Koizumi, H. Okai and T. Kato (1987) Bull. Chem. Soc. Jpn., 60, 2409 (Journal of the Chemical Society of Japan)).

Dodecanedicarboxylic acid (2.5 mmol) and DSP (5 mmol) were dissolved in acetonitrile (35 ml) at 60° C., and after cooling, dicyclohexylcarbodiimide (DCC) (5 mmol) was added and the mixture was stirred at 25° C. for 5 hours. The dicyclohexylurea (DC-Urea) produced during the reaction was removed by filtration with a glass filter. The reaction mixture (filtrate) was added dropwise to ether (70 ml) to solidification. The solid was dried under reduced pressure to obtain 1.4 g of water-soluble crosslinking agent [A] of the invention. The purity of the obtained crosslinking agent was 98% as determined by $^1$H-NMR (JNM-EX-500, JEOL).

Example 8

Fabrication of Molded Elastin Article Using Water-Soluble Crosslinking Agent [A] Obtained in Example 7 as Crosslinking Agent A 200 mg portion of the water-soluble elastin obtained in Example 1 was added to 1 ml of deionized water and the mixture was thoroughly stirred to obtain a 20% water-soluble elastin aqueous solution. The temperature of the aqueous solution was adjusted to 25° C., 72 μmol of the water-soluble crosslinking agent [A] obtained in Example 7 was added (at 3-fold based on the amino groups (25 μmol) of the elastin in the aqueous solution), and the mixture was stirred for 5 minutes. Next, 24 μmol of triethylamine was added, and the mixture was further stirred for 5 minutes and then cast into a cylindrical template with a 2 mm diameter and 2 cm length and allowed to stand for 2 days to produce a gel, which was then thoroughly washed with deionized water to obtain a milky white, highly elastic, cylindrical molded elastin article. The obtained molded elastin article was treated in an autoclave at 110° C. for 10 minutes to obtain a sterilized molded elastin article exhibiting no change in shape. Table 2 shows the results of measuring the Young's modulus of the molded elastin article with a tensile strength tester. The measurement was conducted with the molded elastin article immersed in water. FIG. 1 shows a 90× magnification of a cross-section of the obtained molded elastin article taken with a scanning electron microscope. The electron micrograph shows that the internal structure of the crosslinked elastin was a porous sponge structure with pores having a mean diameter of 62 μm. The elastic moduli of crosslinked elastin products with different pores are shown in Table 2

TABLE 2

| Gel formation temperature | Elastic modulus (25° C.) | Elastic modulus (50° C.) |
|---|---|---|
| 20° C. | 1.2–3.5 $10^3$ Pa | 1.0–4.0 $10^3$ Pa |
| 50° C. | 1.5–7.8 $10^3$ Pa | 0.7–5.0 $10^3$ Pa |

Example 9

Figure 2:
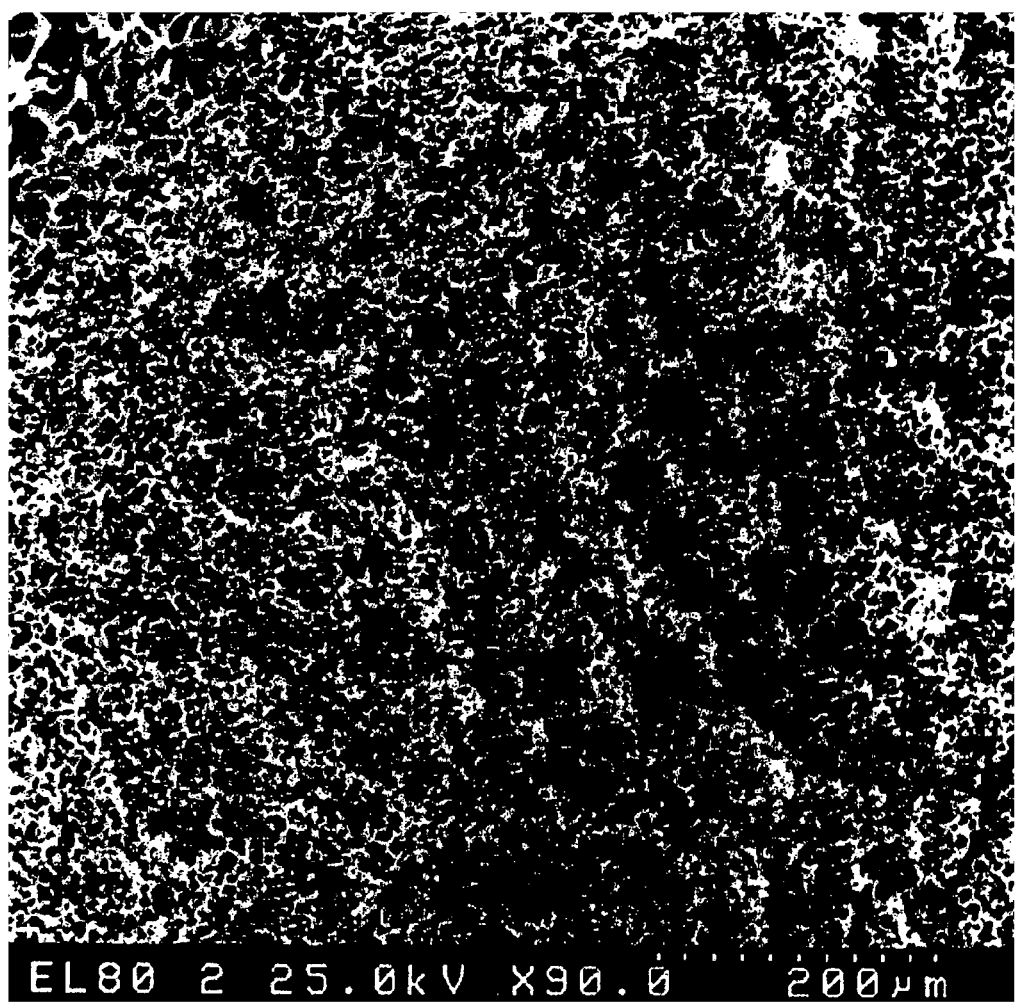
FIG. 2 is an electron micrograph of the crosslinked elastin of the invention according to Example 9 (50° C. reaction).

Fabrication of Molded Elastin Article Using Water-Soluble Crosslinking Agent [A] Obtained in Example 7 as Crosslinking Agent, Under Different Crosslinking Conditions Crosslinking reaction and molding were carried out in the same manner as Example 8, except that the temperature of the aqueous solution was adjusted to 50° C. and the standing time was 6 hours, to obtain a milky white, highly elastic, cylindrical molded elastin article. Table 2 shows the results of measuring the Young's modulus of the molded elastin article with a tensile strength tester. The measurement was conducted with the molded elastin article immersed in water. FIG. 2 shows a 90× magnification of a cross-section of the obtained molded elastin article taken with a scanning electron microscope. The electron micrograph shows that the internal structure of the crosslinked elastin was a porous sponge structure with pores having a mean diameter of 9 µm.

Example 10

Production of Crosslinked Elastin with Elastin Content of 1% of Total, and Fabrication of Molded Article)

Figure 3:
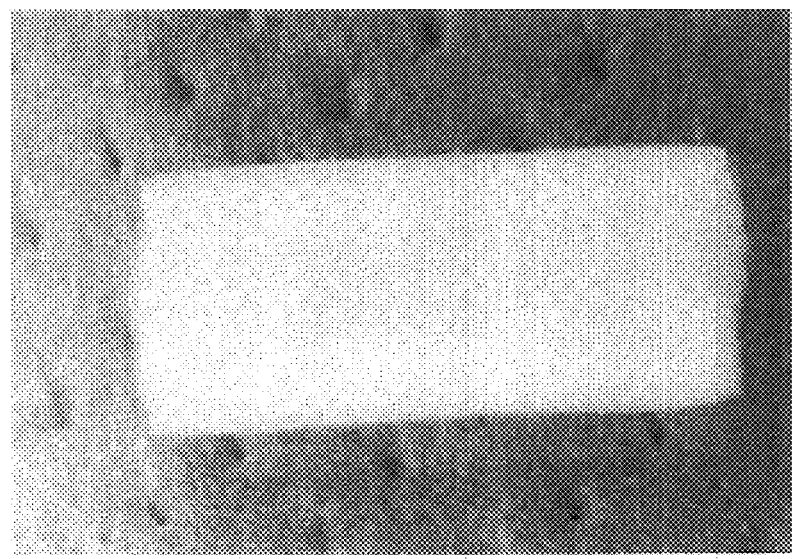
FIG. 3 is an image showing the 1% elastin/gelatin molded crosslinked article of Example 10.

After adding and dissolving 0.8 mg of the water-soluble elastin obtained in Example 1 and 72 mg of gelatin in 148 µl of deionized water, 39 µl (278 mM) of the water-soluble crosslinking agent prepared in Example 7 was added (the amount of crosslinking agent corresponded to a 2-fold amount with respect to the amino groups of the elastin) to prepare a 30% water-soluble elastin aqueous solution. The solution was cast into a molding die and heated with an autoclave at 120° C. for 30 minutes to obtain crosslinked elastin and a molded article thereof (FIG. 3).

Example 11

Figure 4:
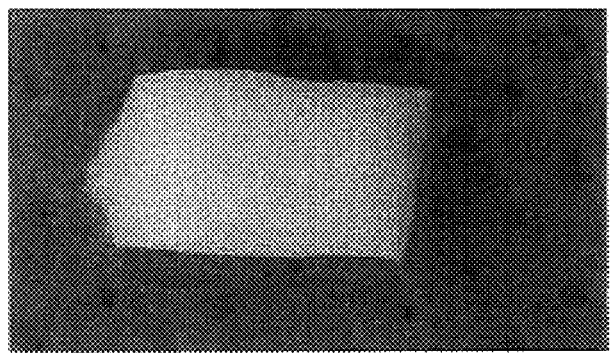
FIG. 4 is an image showing the 10% elastin/gelatin molded crosslinked article of Example 11.

Production of Crosslinked Elastin with Elastin Content of 10% of Total, and Fabrication of Molded Article After adding and dissolving 8 mg of the water-soluble elastin obtained in Example 1 and 72 mg of gelatin in 148 µl of deionized water, 39 µl (278 mM) of the water-soluble crosslinking agent prepared in Example 7 was added (the amount of crosslinking agent corresponded to a 2-fold amount with respect to the amino groups of the elastin) to prepare a 30% water-soluble elastin aqueous solution. The solution was cast into a molding die and heated with an autoclave at 120° C. for 30 minutes to obtain crosslinked elastin and a molded article thereof (FIG. 4).

Example 12

Figure 5:
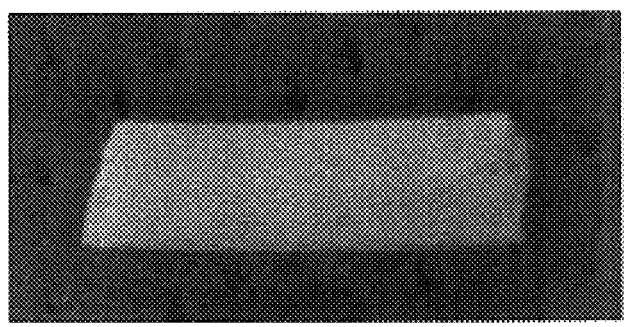
FIG. 5 is an image showing the 90% elastin/gelatin molded crosslinked article of Example 12.

Production of Crosslinked Elastin with Elastin Content of 90% of Total, and Fabrication of Molded Article After adding and dissolving 72 mg of the water-soluble elastin obtained in Example 1 and 8 mg of gelatin in 148 µl of deionized water, 39 µl (278 mM) of the water-soluble crosslinking agent prepared in Example 7 was added (the amount of crosslinking agent corresponded to a 2-fold amount with respect to the amino groups of the elastin) to prepare a 30% water-soluble elastin aqueous solution. The solution was cast into a molding die and heated with an autoclave at 120° C. for 30 minutes to obtain crosslinked elastin and a molded article thereof (FIG. 5).

Example 13

Figure 6:
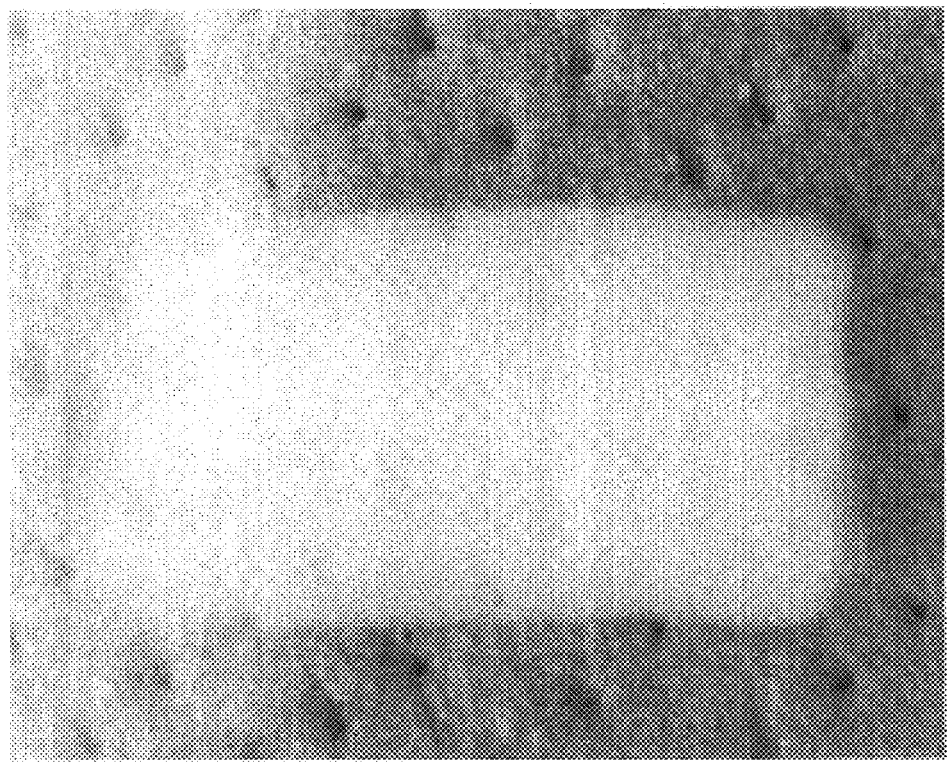
FIG. 6 is an image showing the 0% elastin/gelatin molded crosslinked article of Example 13.

Production of Crosslinked Gelatin with Elastin Content of 0% of Total, and Fabrication of Molded Article After adding 148 µl of deionized water to 80 mg of gelatin to dissolve it, 39 µl (278 mM) of the water-soluble crosslinking agent prepared in Example 7 was added (the amount of crosslinking agent corresponded to a 2-fold amount with respect to the amino groups of the elastin) to prepare a 30% water-soluble elastin aqueous solution. The solution was cast into a molding die and heated with an autoclave at 120° C. for 30 minutes to obtain crosslinked elastin and a molded article thereof (FIG. 6).

Figure 7:
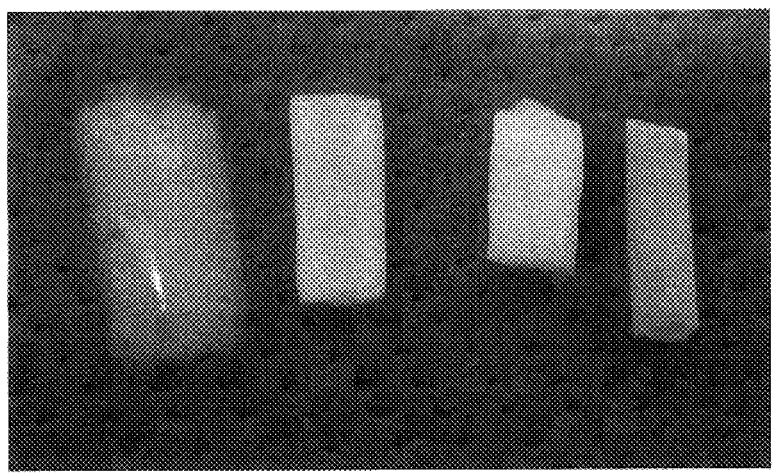
FIG. 7 is a set of comparative images of 0–90% elastin/gelatin molded crosslinked articles.

To summarize the results of Examples 10 to 13, the degree of swelling was high with an elastin content of 0% (swelling to about 2.3 times the diameter of the template after 6 hours in water), but firm-shaped gels were only produced beginning with a content of 1% (FIG. 7: elastin contents of 0, 1, 10 and 90%). The degrees of swelling of the other gels were about 1.5 times the template with the 1% gel, about 1.4 times the template with the 10% gel and about 1.1 times the template with the 90% gel.

The shape stability was higher with a higher elastin content. Upon stretching, the elastic modulus was undetermined but the lower content gels were more easily torn and exhibited low strength.

The gel is colored in yellow in proportion to the increased content of the water-soluble crosslinking elastin solution, which is yellow.

Example 14

Figure 8:
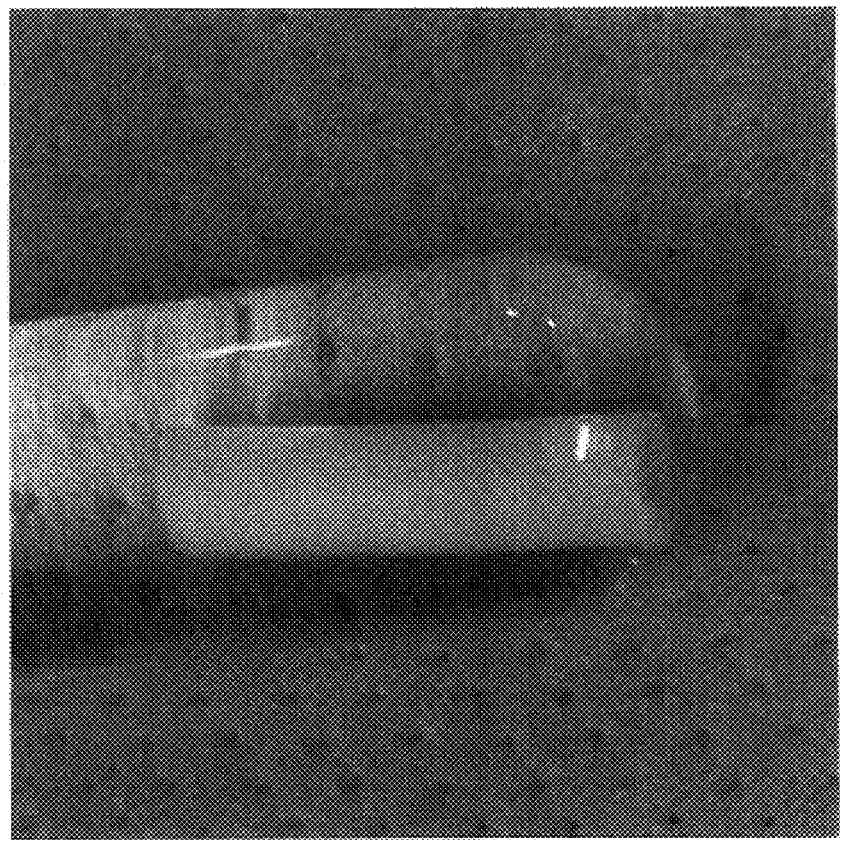
FIG. 8 is an image showing the heparin-containing elastin molded crosslinked article of Example 14.

Production of Crosslinked Elastin with Sugar Also Contained in the Crosslinking Starting Material, and Fabrication of Molded Elastin Article After adding and dissolving 75 mg of the water-soluble elastin obtained in Example 1 and 5 mg of heparin in 148 µl of deionized water, 39 µl (278 mM) of the water-soluble crosslinking agent prepared in Example 7 was added (the amount of crosslinking agent corresponded to a 2-fold amount with respect to the amino groups of the elastin) to prepare a 30% water-soluble elastin aqueous solution. The solution was cast into a molding die and heated with an autoclave at 120° C. for 30 minutes to obtain crosslinked elastin and a molded article thereof (FIG. 8).

Example 15

Confirmation of Heparin Content

Figure 9:
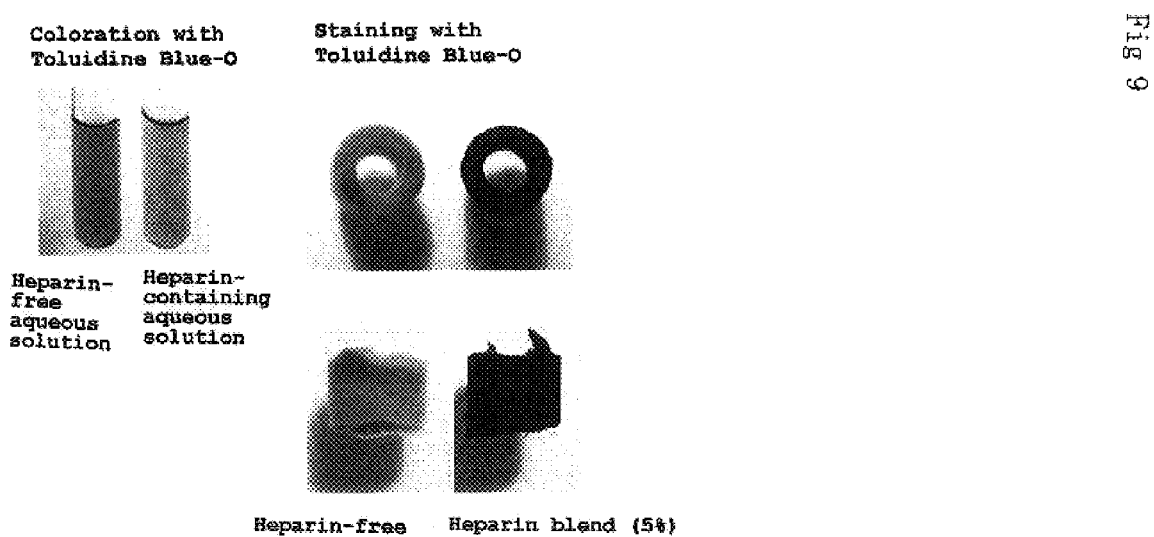
FIG. 9 is a set of images showing the heparin content confirming test of Example 15.

After thoroughly washing the prepared gel with deionized water, it was stained with a 1% Toluidine Blue-O aqueous solution. Toluidine Blue-O stains from blue to violet upon binding with heparin. As shown in FIG. 9, incorporation of heparin in the gel was confirmed.

Example 16

Fabrication of Elastin Membrane

Figure 10:
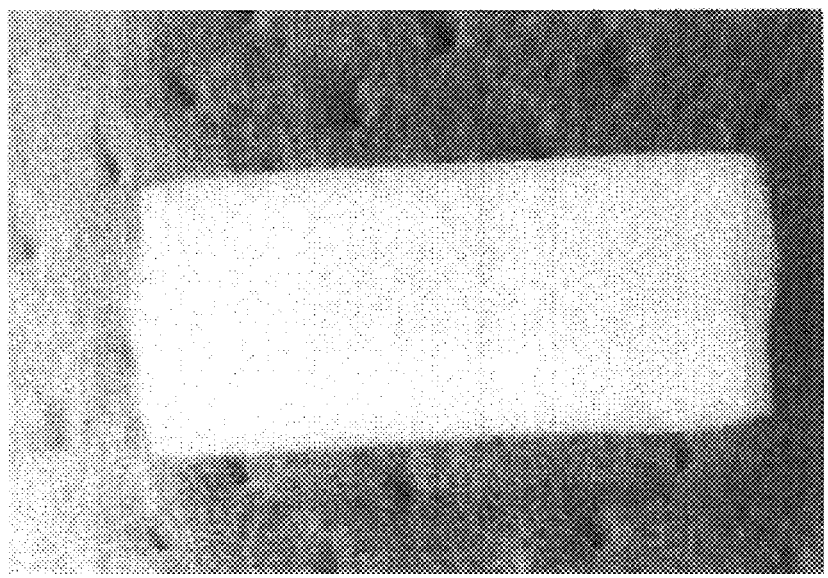
FIG. 10 is an image showing the sheet-like crosslinked elastin of Example 16.

Two Lypersilane-treated (silicone-coated) glass slides were used to prepare a molding die having a silicone rubber sheet as a spacer, and a mixed solution comprising the 30% water-soluble elastin aqueous solution obtained in Example 1 and the water-soluble crosslinking agent prepared in Example 7 (in a 3-fold molar ratio with respect to the elastin amino groups) was cast without allowing entrance of air or water from the outside. These conditions were maintained while heat treatment was carried out in water at 80° C. for 30 minutes, to obtain an elastin membrane (FIG. 10).

Example 17

Production of Different Molded Elastin Articles

Figure 11:
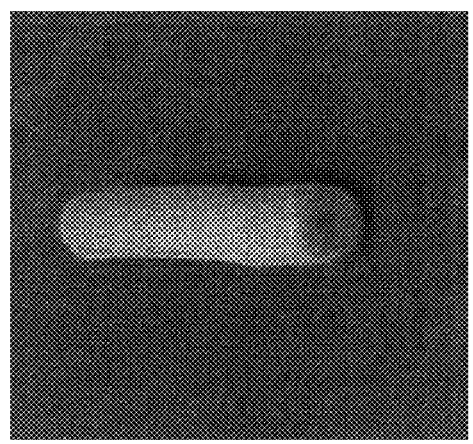
FIG. 11 is an image showing the sheet-like crosslinked elastin of Example 17.
Figure 12:
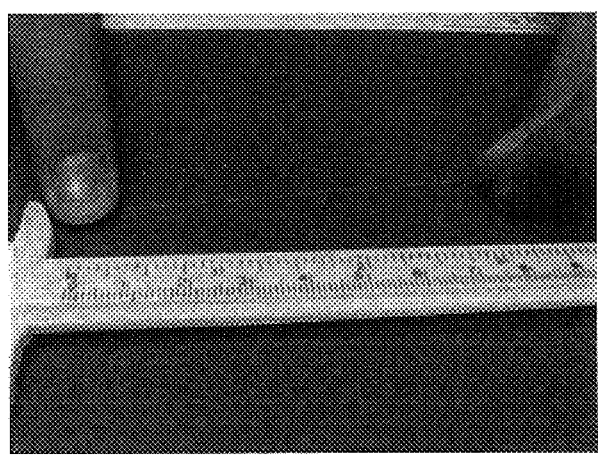
FIG. 12 is an image showing the filamentous crosslinked elastin of Example 17.
Figure 13:
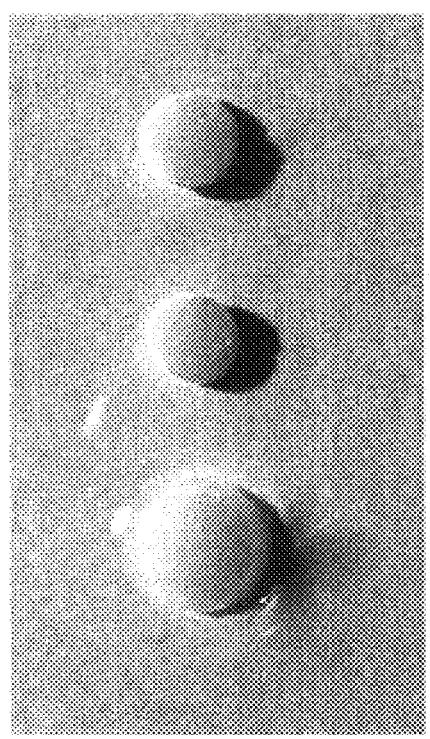
FIG. 13 is an image showing the pelleted crosslinked elastin of Example 17.

Different molding dies were prepared and a mixed solution comprising the 30% water-soluble elastin aqueous solution and the water-soluble crosslinking agent prepared in Example 7 (in a 3-fold molar ratio with respect to the elastin amino groups) was cast without allowing entrance of air or water from the outside. These conditions were maintained while heat treatment was carried out in water at 80° C. for 30 minutes, to obtain tubular (FIG. 11), filamentous (FIG. 12) and pelleted (FIG. 13) molded articles.

Example 18

Cell Culturing Method and Growth Rates

An elastin membrane (0.5 mm thickness, 1 cm×1 cm) was placed on a plastic tissue culturing plate (6 wells), and 2 ml of culture solution was added thereto and stationed at 37° C. for 30 minutes. The culture solution was prepared by adding 215 ml of deionized water to 2.57 g of MEM Hanks' powder to dissolution and then adding 1.17 ml of sodium bicarbonate solution (7.5%), 2.5 ml of glutamine solution (200 mM) and 2.5 ml of non-essential amino acid solution, and finally adding 5 ml of gentamicin and 25 ml of fetal bovine serum.

Next, 100 µl of neuroblastoma cells (IMR-32, ATCC No. CCL-127) were seeded therein to a concentration of 1.0×10$^4$ cells/ml and incubated for 24 hours at 37° C., and the cell count was periodically measured either using a cell counting plate or by direct observation.

As a control, cell growth was evaluated using an albumin coat. The medium was exchanged daily, and the experiment was carried out three times.

Figure 15:
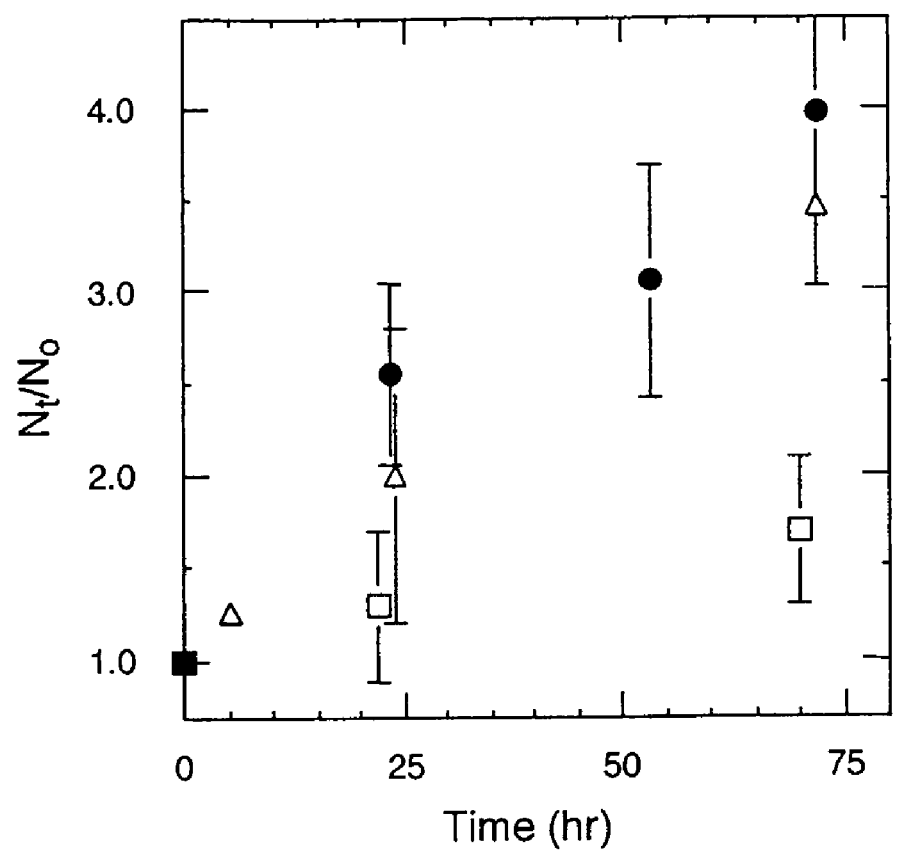
FIG. 15 is an image showing the growth curves of neuroblastomas (IMR-32) on cell adhesion proteins. Δ: gelatin, ⊙: elastin, □: albumin, No: initial cell count on protein-coated culturing plate, Nt: measured cell count.

(Results) The cell growth rate after the 3rd day from seeding of the cells in the elastin (sheet) was approximately 4-fold. With the albumin coat, the cell growth rate after the 3rd day from seeding of the cells was only about 1.5-fold. The growth curve is shown in FIG. 15.

Example 19

Elastin Gel Containing Fibroblast Growth Factor (FGF) and Heparin

Figure 14:
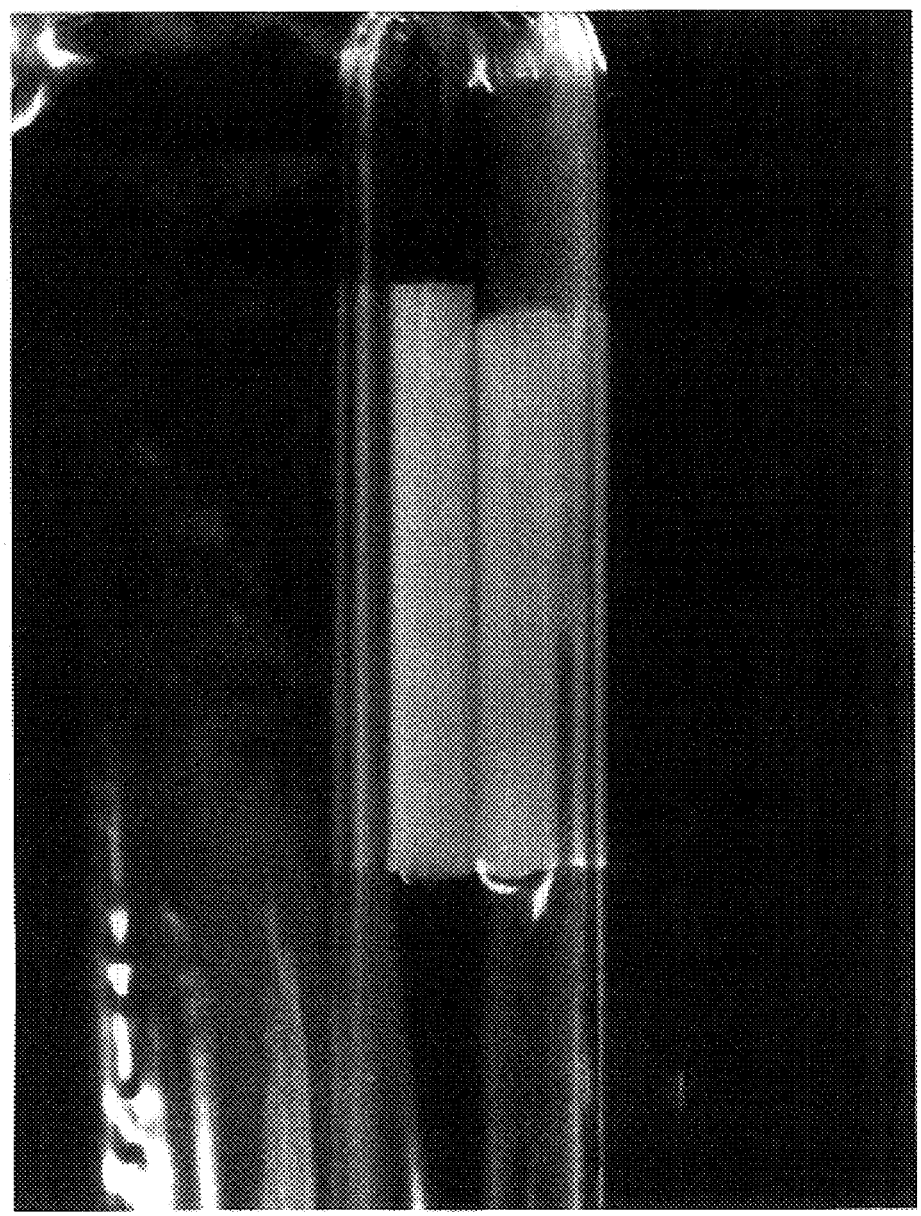
FIG. 14 is an image showing the fibroblast growth factor-containing crosslinked elastin/heparin of Example 19.

After adding 148 1 µl of deionized water to 75 mg of water-soluble elastin and 5 mg of heparin to dissolution, 39 µl (278 mM) of the water-soluble crosslinking agent prepared in Example 7 was added to prepare a 30% elastin aqueous solution. The solution was cast into a molding die and heated at 120° C. (autoclave) for 30 minutes for reaction. The produced gel was washed with a 0.1 M phosphate buffer solution (pH 7.5) and then immersed for 24 hours in a 0.1 M phosphate buffer solution (pH 7.5) containing 2 µg/ml basic fibroblast growth factor (bFGF), for adsorption onto the heparin in the gel. The obtained molded article is shown in FIG. 14.

INDUSTRIAL APPLICABILITY

The crosslinked elastin of the present invention is a material with elasticity suitable for transplantation into the body without detachment of coated cell adhesion proteins, and therefore provides an effect which solves the problems associated with prior art materials whereby cell adhesion proteins become detached with prolonged treatment or whereby regeneration of tissues such as nerves or blood vessels is inadequate.

Moreover, the water-soluble crosslinking agent of the invention crosslinks water-soluble elastin to yield crosslinked elastin with elasticity which permits molding into any shape of a die, and therefore molded articles may be made into filamentous, membranous, cylindrical, pelleted or tubular shapes or worked into regeneration treatment materials or medical instrument materials, as an effect allowing its application for a wide range of uses.

Furthermore, since the crosslinked elastin of the invention forms a porous sponge structure, it allows permeation of drugs and the like and facilitates formation of composites with other materials, as an effect to allow provision of new medical materials.

The invention claimed is:

1. A crosslinked elastin comprising a crosslinking starting material containing at least one type of water-soluble elastin crosslinked with a water-soluble crosslinking agent selected from the group consisting of compounds represented by the following general formula:

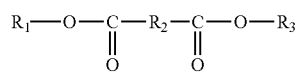

wherein $R_1$ and $R_3$ are each A or B represented by the following structural formulas and $R_1$ and $R_3$ may be the same or different:

A

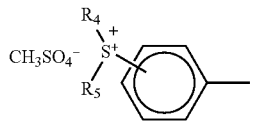

wherein $R_4$ and $R_5$ are each H, $CH_3$ or $C_2H_5$, and $R_4$ and $R_5$ may be the same or different;

B

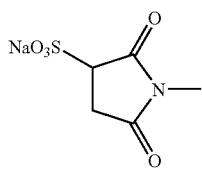

and $R_2$ is C or D represented by the following structural formulas:

C

wherein n is an integer from 1–20;
and

D

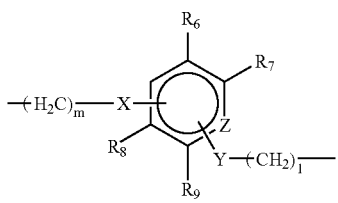

wherein m and l are each an integer from 0–15, X and Y are each $CH_2$ or O and X and Y may be the same or different, Z is C or N, and $R_6$, $R_7$, $R_8$ and $R_9$ are each H, $CH_3$ or $C_2H_5$ and may be the same or different.

2. A composition comprising a crosslinked elastin according to claim 1, wherein the crosslinking starting material further comprises at least one component selected from the group consisting of: collagen, gelatin, fibronectin, fibrin, laminin, casein, keratin, sericin, thrombin, polyglutamic acid, polylysine, polygalacturonic acid, heparin, chondroitin sulfate, hyaluronic acid, dermatan sulfate, chondroitin, dextran sulfate, sulfated cellulose, alginic acid, dextran, carboxymethylchitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan, lentinan, bFGF (basic Fibroblast Growth Factor), TGF-α (Transforming Growth Factor α), EGF (Epidermal Growth Factor), VEGF (Vascular Endothelial Growth Factor), CNTF (Ciliary NeuroTrophic Factor), as polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid.

3. A crosslinked elastin according to claim 1, wherein the water-soluble elastin content is in the range of 0.5–99.5 wt %.

4. A crosslinked elastin according to claim 1, wherein the Young's modulus is in the range of $1\times10^2$ to $1\times10^7$ Pa.

5. A crosslinked elastin according to claim 1, wherein the internal structure is a porous sponge structure.

6. A crosslinked elastin according to claim 5, wherein the mean diameter of the pores is less than 20 μm.

7. A crosslinked elastin according to claim 5, wherein the mean diameter of the pores is in the range of 20 μm to 2 mm.

8. A composition according to claim 2, wherein the at least one component selected from the group consisting of collagen, gelatin, fibronectin, fibrin, laminin, casein, keratin, sericin, thrombin, polyglutamic acid, polylysine, polygalacturonic acid, heparin, chondroitin sulfate, hyaluronic acid, dermatan sulfate, chondroitin, dextran sulfate, sulfated cellulose, alginic acid, dextran, carboxymethylchitin, galactomannan, gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan, lentinan, bFGF (basic Fibroblast Growth Factor), TGF-α (Transforming Growth Factor α), EGF (Epidermal Growth Factor), VEGF (Vascular Endothelial Growth Factor), CNTF (Ciliary NeuroTrophic Factor), polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid, are chemically bonded.

9. A composition according to claim 8, wherein the chemical bond is a crosslink produced using a crosslinking agent.

10. A composition comprising a crosslinked elastin according to claim 1, further comprising at least one component selected from the group consisting of: collagen, gelatin, fibronectin, fibrin, laminin, casein, keratin, sericin, thrombin, polyglutamic acid, polylysine, polygalacturonic acid heparin, chondroitin sulfate, hyaluronic acid, dermatan sulfate, chondroitin, dextran sulfate, sulfated cellulose, alginic acid, dextran, carboxymethylchitin, galactomannan gum arabic, tragacanth gum, gelan gum, sulfated gelan, karaya gum, carrageenan, agar, xanthan gum, curdlan, pullulan, cellulose, starch, carboxymethyl cellulose, methyl cellulose, water-soluble soybean polysaccharide, glucomannan, chitin, chitosan, xyloglucan lentinan, bFGF (basic Fibroblast Growth Factor), TGF-α (Transforming Growth Factor α), EGF (Epidermal Growth Factor), VEGF (Vascular Endothelial Growth Factor), CNTF (Ciliary NeuroTrophic Factor), polymethyl methacrylate, polydimethylsiloxane, polytetrafluoroethylene, silicone, polyurethane, polyethylene terephthalate, polypropylene, polyethylene, polycaprolactone, polypropylene ether, polytetramethylene glycol, polyethylene glycol, polylactic acid, polyvinyl alcohol and polymalic acid.

11. A composition comprising a crosslinked elastin according to claim 1, wherein the crosslinking starting material further comprises at least one component selected from the group consisting of: proteins, polyaminoacids, sugars, and cell growth factors.

12. A composition according to claim 11, wherein said at least one component selected from the group consisting of: proteins, polyaminoacids, sugars, and cell growth factors, are chemically bonded.

13. A composition comprising a crosslinked elastin according to claim 1, further comprising at least one component selected from the group consisting of: proteins, polyaminoacids, sugars, and cell growth factors, are chemically bonded.

* * * * *